United States Patent [19]

Valli

[11] 4,437,856
[45] Mar. 20, 1984

[54] PERITONEAL CATHETER DEVICE FOR DIALYSIS

[76] Inventor: Alberto Valli, Via Cappelletta, 29, Cogliate (Province of Milano), Italy

[21] Appl. No.: 232,495

[22] Filed: Feb. 9, 1981

[51] Int. Cl.³ .................. A61M 25/00; A61M 1/03
[52] U.S. Cl. ............................. 604/29; 604/43; 604/96
[58] Field of Search ................... 128/241–246, 128/348–350, 344, 213 A; 604/27–29, 43, 96

[56] References Cited

U.S. PATENT DOCUMENTS

| | | | |
|---|---|---|---|
| 2,470,665 | 5/1949 | Stiehl | 128/348 X |
| 2,650,592 | 9/1953 | Borda | 128/242 |
| 3,173,418 | 3/1965 | Baran | 128/349 B |
| 3,512,517 | 5/1970 | Kadish et al. | 128/635 |
| 3,640,269 | 2/1972 | Delgado | 128/348 X |
| 3,888,249 | 6/1975 | Spencer | 128/348 X |
| 4,184,497 | 1/1980 | Kolff et al. | 128/213 A |
| 4,235,231 | 11/1980 | Schindler et al. | 604/4 |

FOREIGN PATENT DOCUMENTS

| | | | |
|---|---|---|---|
| 626849 | 10/1961 | Italy | 128/349 B |

*Primary Examiner*—Dalton L. Truluck
*Attorney, Agent, or Firm*—Guido Modiano; Albert Josif

[57] ABSTRACT

A peritoneal catheter device for dialysis comprises a rigid catheter wherearound a membrane is arranged which is permeable for a dialysing liquid and shaped to a substantially balloon-like shape by application of a pressure, such as to expand the area reached by the dialysing liquid.

4 Claims, 9 Drawing Figures

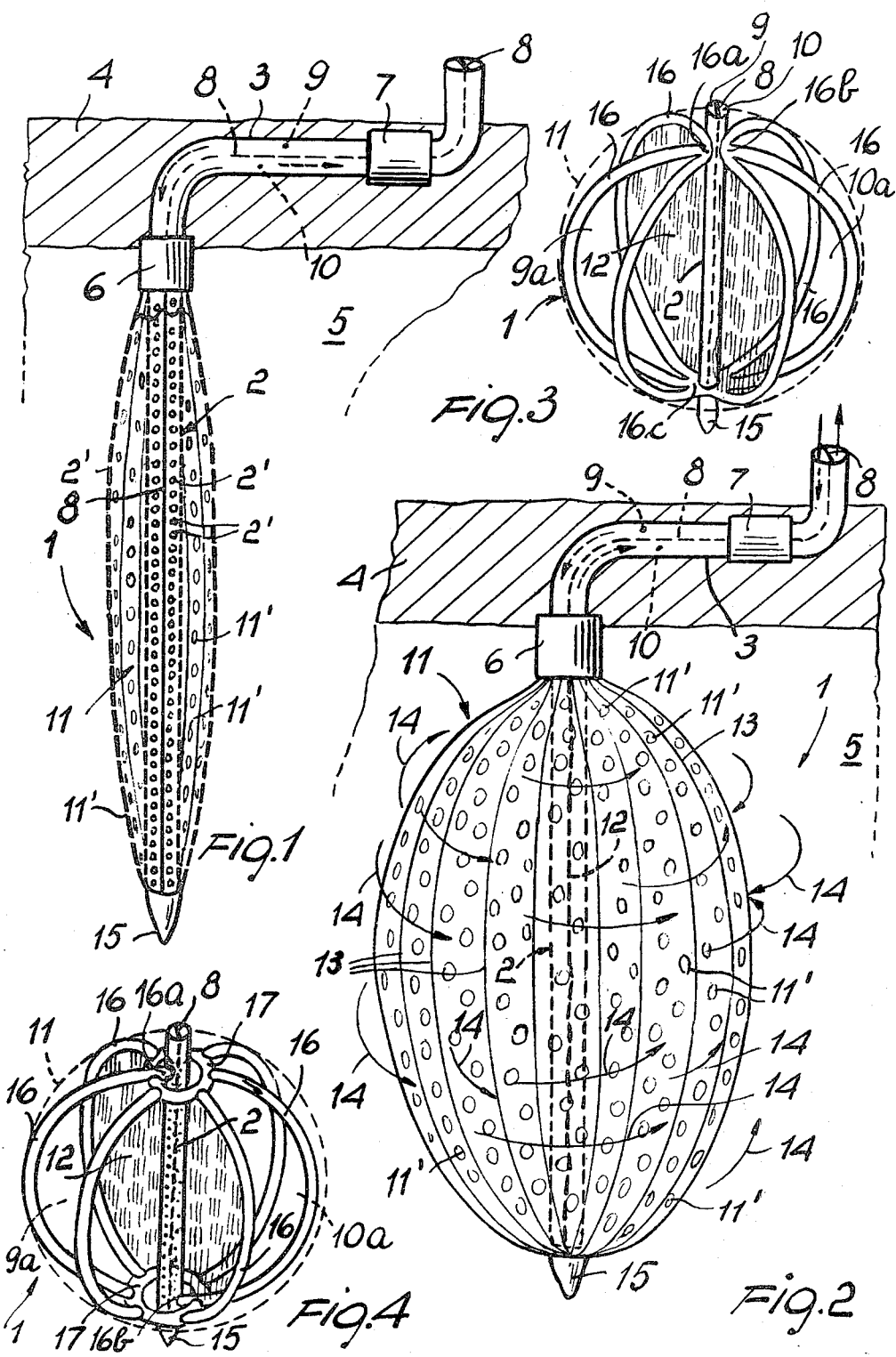

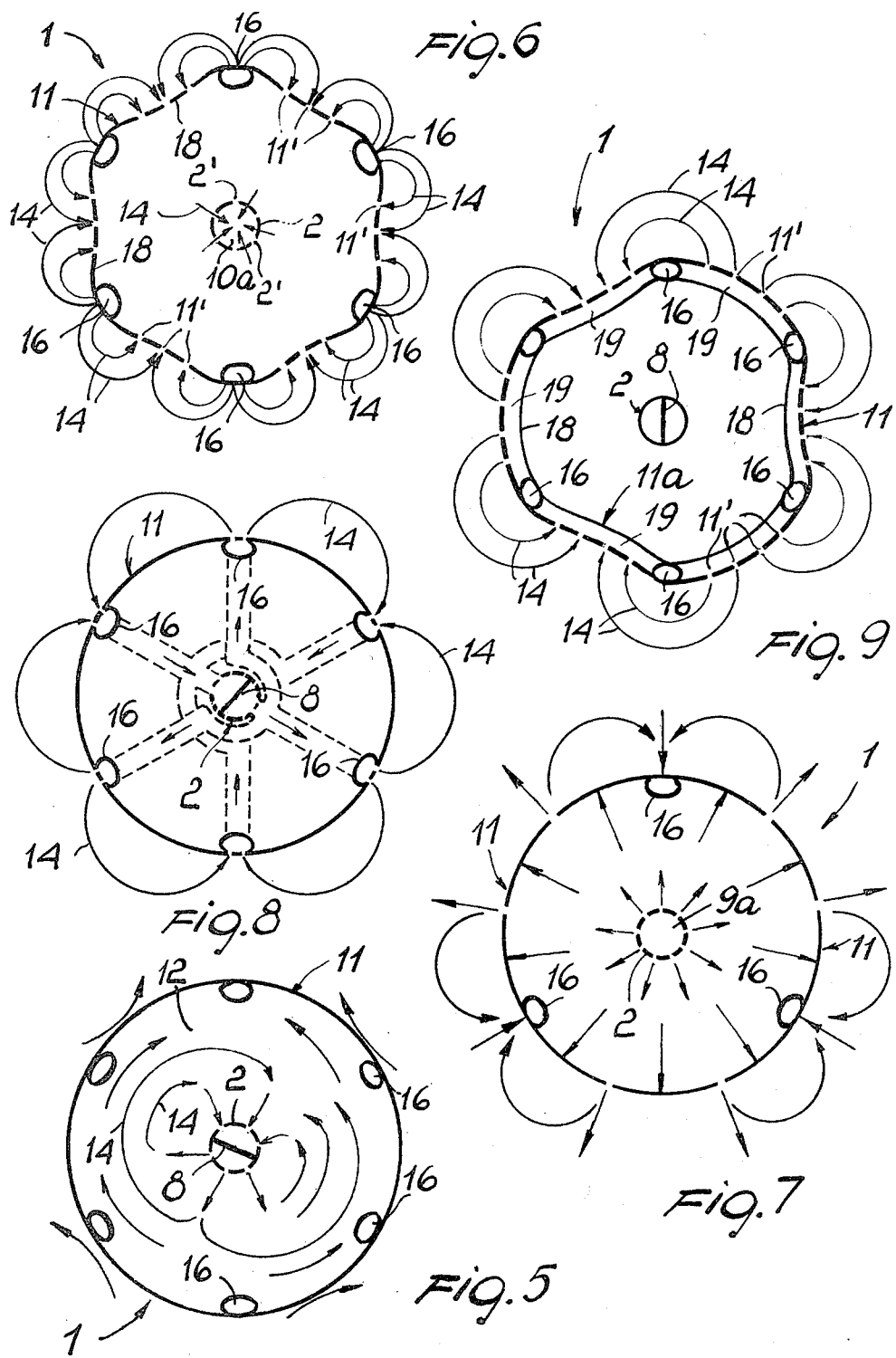

PERITONEAL CATHETER DEVICE FOR DIALYSIS

BACKGROUND OF THE INVENTION

This invention relates to a peritoneal catheter device for dialysis or the like treatments in the abdominal cavity.

Peritoneal catheters for dialyses have been known and used alternatively to the extra-corporal dialysis. As an example, known is a peritoneal catheter for chronic peritoneal dialysis, which is denoted "Torelli-Valli" from its inventors. Said catheter comprises essentially a perforated cylindrical rod, hollow inside, which is connected to equipment operative to introduce a dialysing liquid into it. The operation mode of that peritoneal catheter provides for the insertion of the same, either in a permanent or semi-permanent way, within the abdominal cavity, and the intermittent delivery of a dialysing liquid to the catheter. The dialysing liquid enters the abdominal cavity through holes formed in the catheter wall, and is withdrawn from the abdominal cavity through those same holes, thereby its operation cycle is a discontinuous and alternating one.

Inside the abdominal cavity, the dialysing liquid will effect the required interchange with blood at the abdominal capillaries which, in this case, take the place of the filtering membranes employed in extra-corporal dialyses.

To achieve maximum dialysis effectiveness, it is expedient for the dialysing liquid to intimately contact all of the abdomen recesses, including bends, to thereby increase as mush as possible the amount of blood exchanging, through the semipermeable membranes of the capillary vessels, and by osmosis or diffusion, its substances to be purified with the purifying substance contained in the dialysing liquid.

The process just described has the very important advantages of utilizing for the semipermeable membranes those naturally provided by the human body, instead of artificial ones, and that no blood is drawn off the normal circulatory system. Furthermore, the same dialysing liquids can be used as in extra-corporal dialysis.

Such significant advantages bring about further a significant simplification of the dialysis promoting equipment, which is only required to renew the dialysing liquid, and of the procedure, as well as in lower patient treatment costs, so that a higher number of patients can be treated.

However, the above advantages are somewhat counteracted by certain limitations. In fact, the available exchange surface area is, in conventional devices, restricted because defined by the surface areas of the blood vessels located in the neighborhood of the catheter. Quite serious is then the reduction of the dialysis efficiency which results from the aforementioned discontinuous and alternating type of operation, which involves both idle time and the need to let the dialysing liquid flow twice through one abdomen portion, with the attendant risk that the direction of the reactions is reversed.

An added drawback of conventional catheters is that their outflow and inflow ports are likely to become clogged owing to the catheter being positioned in close contact with intestine bends.

SUMMARY OF THE INVENTION

In view of the situation outlined hereinabove, this invention sets out to reduce the drawbacks and limitations affecting conventional catheters, by providing a novel catheter device which affords a faster operation and affects a larger area than was hitherto feasible.

A further object of the invention is to provide a catheter device, which while enabling higher flow rates and longer paths for the dialysing liquid through the peritoneal cavity, as well as a continuous and clog-free process, has insertion sections and a length which are not substantially greater than those of currently known catheters.

These and other objects, such as may be brought forth hereinafter, are all achieved, according to the invention, by a peritoneal catheter device for dialysis of the type wherein a perforated wall rigid catheter is inserted into a body cavity, and the dialysing liquid is delivered and drawn through the catheter perforations into and from the body cavity, characterized in that around said rigid catheter there is arranged a membrane which is permeable for said dialysing liquid or shaped to a substantially balloon-like shape by application of a pressure, such as to expand the region that can be reached by said dialysing liquid.

BRIEF DESCRIPTION OF THE DRAWINGS

The invention will be presently explained and illustrated in every aspects thereof, by describing preferred, but not limitative, embodiments thereof, with reference to the accompanying drawings, where:

FIG. 1 illustrates the catheter device according to the invention, in a prevailingly sectional side elevation, in the condition where it is inserted into and attached to an abdomen area;

FIG. 2 shows the same device as in FIG. 1, in the inflated condition thereof;

FIGS. 3 and 4 are schematical partially transparent views of two variations of the internal structure of the device of FIG. 2, in the inflated condition thereof; and FIGS. 5 to 9 show schematically and in equatorial cross-section further embodiments of the device according to this invention.

DESCRIPTION OF THE PREFERRED EMBODIMENTS

With reference in particular to FIGS. 1 and 2, there is generally indicated at 1 a catheter device according to the invention. It comprises a catheter 2 proper, which is rigid and cylindrical and has a perforated wall, as at 2', it being of a type known per se. To the catheter 2, there is connected at the proximal end thereof a supply and discharge tube 3 which puts the catheter 2 into communication with the outside of the human body through a cutaneous layer 4, the catheter being positioned inside the intestine or peritoneal cavity 5. Two germ barriers 6 and 7, e.g. formed from Dacron, which are sealed both to the synthetic material of the tube 3 and to the tissue of the layer 4, are wrapped around the tube 3 and secure it elastically such as to block any sliding movements. Both the tube 3 and catheter 2 are divided longitudinally by a centrally located or diametrical partition or septum 8 which defines two conduits: a delivery one 9, and a return one 10.

The basic characteristic of the invention resides in the provision of a folding and inflatable membrane 11 which surrounds the catheter 2 throughout its length and is attached to the two ends thereof i.e. the distal and proximal ends. In FIGS. 1 to 4, the membrane 11 is sealingly divided by a flexible wall 12 aligned with the septum 8 of the catheter 2, which defines two separate chambers for the dialysing liquid: a delivery chamber 9a and return chamber 10a. The membrane 11 is preferably formed from meridian sectors 13, which can be folded to a pleated form, to adhere more closely to the catheter 2 and form a thin spindle around it, as shown in FIG. 1, or form a balloon or the like, as shown in FIG. 2.

The technical solution shown in FIGS. 1 and 2 provides for a substantially impermeable material membrane 11 which has holes 11' for the passage of the dialysing liquid.

The catheter device can be inserted as a whole into the patient's body, preferably into the peritoneal cavity, e.g. through a tip 15 provided at the distal end of the catheter 2 outwardly of the membrane 11. The provision of the tip or nosepiece 15 enables the catheter device 1 to be handled like a trocar and an insertion guided by the operator's tactile sensitivity. Alternatively, the catheter device can be inserted into the patient's body through a small marginal implantation and plastic intervention.

Preferably, after inserting the device 1 and after the barriers 7 have been fixed, the dialysing action begins simultaneously with the inflation of the membrane 11, since it is the dialysing liquid itself, as delivered under pressure through the catheter 2, that expands the membrane 11, while flowing out through the holes 11' of the latter and establishing within the peritoneal cavity, at a position spaced from the catheter 2, a circulation as indicated by the arrows 14. It will be appreciated that the holes 11' are equivalent to perforations defining means.

The diameters and number of the holes 11' may be selected such that the dialysing liquid delivered at the operating flow rate creates a sufficient pressure to expand the membrane 11 at preestablished portions. However, even though it is possible to simply utilize the pressure of the dialysing liquid itself, which is free within the membrane 11, to expand or inflate the membrane, it is preferable to employ different technical solutions to accomplish the expansion of the membrane 11 independently of the flow rate of the dialysing liquid.

FIGS. 3 and 4 illustrate two preferred technical solutions which are similar to each other, for expanding the membrane 11. In both such technical solutions, the membrane has on the inside tubular meridian ribs 16 which, when subjected to the pressure of a liquid, behave as supports, to impart to the membrane a final shape which is almost independent of its internal pressure.

In particular, the meridian ribs 16 of FIG. 3 extend along the entire circumference of the membrane 11, when the latter is inflated balloon-like. These ribs have an entrance 16a at said delivery conduit 9 of the tube 3 and catheter 2, and a discharge 16b at the return conduit 10. In practice, the circumferential ribs 16 converge into the same portion of the catheter 2 but at opposite sides with respect to the septum 8. Advantageously, the ribs 16 can be connected together by a confluence region 16c arranged adjacent the tip or nose 15. The provision of this confluence region also enables the ribs 16 to be arranged semi-circumferentially only, and not aligned to one another. As an example, it is possible to provide no more than two ribs 16 at said delivery chamber 9a, within the membrane 11, because the delivery chamber is already spontaneously inflated by the dialysing fluid, and more than two ribs 16 at the return chamber 10a.

It will be appreciated that the connections between the ribs 16 and catheter 2 can be variously implemented. FIG. 4 illustrates a further example of an advantageous connection wherein the entrance 16a and discharge 16b are spaced apart from each other: one adjacent the tube 3, the other adjacent the tip or nosepiece 15. In this case, all the ribs 16 must be connected together at said entrance and discharge through headers 17.

In a different embodiment of this catheter device, shown schematically by the equatorial section of FIG. 5, provision is made for the membrane 11 to be of a semipermeable material having no visible perforations. In this case, while the active substances of the dialysing liquid freely pass through the semipermeable membrane to enter the peritoneal liquid which is at all times present in the intestine pouch those germs and bacteria which may contaminate the dialysing liquid introduced into the catheter device remain trapped within the semipermeable membrane. Thus, the likelihood is prevented from the start of any infectious inception, without hindering thereby the dialysis process, since the peritoneal liquid, whereinto the active substances of the dialysing liquid are poured freely, continuously exchanges with the blood through the blood vessels.

Of course, the semipermeable membrane 11 also allows the return passage of the deposits to be discharged, again by diffusive exchange. With this technical solution, it is expedient to continuously renew the dialysing liquid within the membrane 11, by continously introducing the same through the perforations 2' of the delivery conduit 9a of the catheter, and reassuming the dialysing liquid through the perforations 2' of the return conduit 10a of the catheter 2. Suitably, to permit the circulation of the dialysing liquid within the membrane 11, the flexible wall 12 will be omitted.

FIGS. 6 to 9 show, again in equatorial section, further embodiments of the catheter device according to this invention.

In detail, FIG. 6 shows a variation of the invention, wherein the ribs 16, as pressurized by the dialysing liquid, deliver the liquid outwardly through their perforations. The dialysing liquid is re-introduced into the catheter 2 through the perforations of the remaining portions of the membrane 11. The dialysing liquid within the membrane itself, during the return step, is drawn off through all of the perforations or holes 2' of the catheter 2, without the septum 8. Thus, the septum 8 will be only provided in the tube 3 and all the ribs 16 will be connected to the delivery conduit 9a of the tube 3 through a header such as the one shown in FIG. 4. Moreover, the ribs 16 will be terminated adjacent the tip 15, either blind or interconnected together.

FIG. 7 shows a reverse situation with respect to the one of FIG. 6, that is the dialysing liquid is delivered through those portions of the membrane 11 which are included between the ribs 16, and the latter, which are here reduced to three in number, function as collectors for the returning dialysing liquid. In this technical solution, the ribs 16 are still connected to one another through a header which is similar to those shown in FIG. 4, and the header itself will be positioned in communication with the return conduit 10a of the tube 3. Thus, similarly to the example of FIG. 6, the catheter 2 will be without the septum 8.

In FIG. 8, the inflation of the device is again provided, like in FIG. 7, by those portions of the impermeable and unperforated membrane 11 which are included between the ribs 16, the ribs being alternatively dialysing liquid supplying and receiving ribs. The inflation will be accomplished, for example, by providing in the catheter 2 a number of dialysing liquid delivering or supplying holes which is larger than the number of the discharge holes. The ribs 16 will be then connected alternately to the delivery conduit and return conduit in the catheter 2 through headers, e.g. of the type schematically illustrated by the dotted lines of the Figure. These headers may be arranged, as an example, in the neighborhood of the tube 3, and at the opposite end, at the tip or nosepiece 15. The ribs 16 will be blind, or selectively interconnected together: the delivery ribs on one side and the return ribs on the other side.

The technical solution of FIG. 9 provides ribs 16 which are unperforated and pressurized by a liquid or gas, an outer membrane 11, and an inner membrane 11a which is divided into sectors 18 by the ribs 16. The two membranes 11,11a form a plurality of receptacles 19 which can be alternately filled with dialysing liquid as delivered and as collected. The inner membrane 11a may be filled, through independent inlet and outlet conduits, with air, a gas, or a static liquid, to mention but a few. The receptacles 18 may be connected to the catheter 2 in the same manner as shown for the ribs 16 of the technical solution of FIG. 8.

The variety of alternative approaches which have been proposed hereinabove in accordance with the invention demonstrates the high degree of adaptability of this device to special conditions and applicational requirements, without prejudice for the basic advantage of an increased exchange area, as brought about by the presence of the expandable membrane 11. As a general indication, the solution of FIG. 6 may be preferable where specially high flow rates are required in order to increase the rate of exchange. The solution of FIG. 9 shows how it becomes possible to fully separate the dialysing liquid from the pressure liquid. The solution of FIG. 8 is advantageous in that it enables the dialysing liquid to be channeled to completely avoid inner stagnation pockets which in general tend to reduce the efficiency of the exchange process. The solution of FIG. 5 is the one which ensures the utmost degree of safety against infection, or any introduction of dangerous elements into the human body. The technical solution of FIG. 7 is substantially similar to the technical solution of FIG. 6, although the flow of the dialysing liquid is here operatively reversed. Lastly, the basic technical solution, as shown in FIGS. 1 to 4, is the one which most successfully meets the requirements for a strong and amply diffused flow of the dialysing liquid, a reduced clogging of the membrane perforations by the intestine bends, a simple construction, and reliable operation.

The embodiments discussed in the foregoing are the ones which, at the present stage of the research work carried out on the invention, appear to be more objectively promising, but an expert may introduce modifications and variations thereof without departing from the scope of the instant inventive concept.

I claim:

1. A peritoneal catheter device for dialysis comprising a rigid catheter portion of elongated tubular shape having an interior, a length, a distal and a proximal end thereof and a plurality of openings spaced apart from each other along the entire length of the catheter portion, said tubular catheter portion being closed at said distal end and defining a cul-de-sec, a longitudinal partition wall extending within said catheter portion along the entire length thereof and dividing the catheter interior into two separated delivery and discharge conduits, supply and discharge ducts for a dialysing liquid connected at said proximal end of said rigid catheter portion with said separated conduits, an inflatable and expandable membrane generally of tubular shape surrounding said catheter portion throughout its length and fixed near said distal and proximal end to define an expandable chamber between said catheter and said inflatable and expandable membrane adapted to be filled with dialysing liquid, said inflatable membrane having perforations defining means for the passage of said dialysing liquid therethrough and in use expanding to a substantially balloon-like shape, said catheter being adapted in use to be inserted in a body cavity such as the peritoneal cavity between the bends of the intestine to deliver and draw the dialysing liquid through the openings of said catheter.

2. A device according to claim 1, wherein said perforations defining means for delivering or drawing the dialysing liquid into or from the peritoneal cavity are holes.

3. A device according to claim 1, wherein said perforations defining means are in the form of a semipermeable structure.

4. A peritoneal catheter device for dialysis comprising a rigid catheter portion of elongated tubular shape having an interior, a length, a distal and a proximal end thereof and a plurality of openings spaced apart from each other along the entire length of the catheter portion, said tubular catheter portion being closed at said distal end and defining a cul-de-sac, a longitudinal partition wall extending within said catheter portion along the entire length thereof and dividing the catheter interior into two separated delivery and discharge conduits, supply and discharge ducts for a dialysing liquid connected at said proximal end of said rigid catheter portion with said separated conduits, an inflatable and expandable membrane generally of tubular shape surrounding said catheter portion throughout its length and fixed near said distal and proximal end to define an expandable chamber between said catheter and said inflatable and expandable membrane adapted to be filled with dialysing liquid, said rigid catheter portion having a rigid tip at said distal end, said rigid tip being arranged outwardly of said membrane to define a means for guiding insertion of said catheter, and a germ barrier fastened to said rigid catheter portion at said proximal end, said membrane being fixed to said rigid catheter portion between said rigid tip and said germ barrier, said inflatable membrane having perforations defining means for the passage of said dialysing liquid therethrough and in use expanding to a substantially balloon-like shape, said catheter being adapted in use to be inserted in a body cavity such as the peritoneal cavity between the bends of the intestine to deliver and draw the dialysing liquid through the openings of said catheter.

* * * * *